US010631809B2

(12) United States Patent
Noh

(10) Patent No.: US 10,631,809 B2
(45) Date of Patent: Apr. 28, 2020

(54) LIFTING DEVICE FOR COMPRESSION PADDLE AND X-RAY IMAGING APPARATUS INCLUDING THE SAME

(71) Applicants: Rayence Co., Ltd., Gyeonggi-do (KR); VATECH EWOO Holdings Co., Ltd., Gyeonggi-do (KR)

(72) Inventor: Byoung Soo Noh, Gyeonggi-do (KR)

(73) Assignee: Rayence Co., Ltd., Gyeonggi-do (KR)

( * ) Notice: Subject to any disclaimer, the term of this patent is extended or adjusted under 35 U.S.C. 154(b) by 219 days.

(21) Appl. No.: 15/539,823

(22) PCT Filed: Dec. 24, 2015

(86) PCT No.: PCT/KR2015/014234
§ 371 (c)(1),
(2) Date: Jun. 26, 2017

(87) PCT Pub. No.: WO2016/105144
PCT Pub. Date: Jun. 30, 2016

(65) Prior Publication Data
US 2017/0367670 A1    Dec. 28, 2017

(30) Foreign Application Priority Data

Dec. 26, 2014 (KR) .......................... 10-2014-0190616

(51) Int. Cl.
*A61B 6/00* (2006.01)
*A61B 6/04* (2006.01)
(Continued)

(52) U.S. Cl.
CPC ................ *A61B 6/502* (2013.01); *A61B 6/00* (2013.01); *A61B 6/04* (2013.01); *A61B 6/0414* (2013.01);
(Continued)

(58) Field of Classification Search
CPC ......... A61B 6/502; A61B 6/0414; A61B 6/44; A61B 6/56; B66B 7/06; B66B 15/04;
(Continued)

(56) References Cited

U.S. PATENT DOCUMENTS 4,599,738 A * 7/1986 Panetta ................ A61B 6/0414
378/180
4,658,409 A * 4/1987 Summ .................. A61B 6/0414
378/117

(Continued)

FOREIGN PATENT DOCUMENTS

CN    103876760 A    6/2014
EP    2740406 A1    6/2014
(Continued)

OTHER PUBLICATIONS

Patent Translate powered by EPO of the description of CN103876760.*
(Continued)

*Primary Examiner* — David P Porta
*Assistant Examiner* — Djura Malevic
(74) *Attorney, Agent, or Firm* — IP Legal Services, LLC

(57) ABSTRACT

The present invention relates to a lifting apparatus for a pressure paddle, the lifting apparatus for the pressure paddle comprising: a lifting belt rotated by a driving means; a lifting pulley manually rotated by the lifting belt hung thereon; a lifting frame on which the lifting pulley is mounted; and a pressure paddle mounted on the lifting frame.

11 Claims, 9 Drawing Sheets

(51) Int. Cl.
*F16D 27/06* (2006.01)
*H05G 1/26* (2006.01)

(52) U.S. Cl.
CPC ............... *A61B 6/44* (2013.01); *F16D 27/06* (2013.01); *H05G 1/26* (2013.01); *A61B 6/56* (2013.01)

(58) Field of Classification Search
CPC ... F16H 1/16; F16H 1/166; F16H 1/22; F16H 1/225; F16H 9/00; F16H 9/12; F16H 7/02; F16H 7/10; F16H 7/14; F16H 55/52; B62M 9/16
See application file for complete search history.

(56) References Cited

U.S. PATENT DOCUMENTS

| | | | | |
|---|---|---|---|---|
| 5,099,503 A * | 3/1992 | Strommer | ............... | H05G 1/64 378/208 |
| 5,335,257 A * | 8/1994 | Stunberg | ............ | A61B 6/0414 378/117 |
| 5,398,272 A * | 3/1995 | Bouscary | ............... | A61B 6/502 378/208 |
| 5,506,877 A * | 4/1996 | Niklason | ............... | A61B 6/502 378/208 |
| 5,526,394 A * | 6/1996 | Siczek | ................ | A61B 6/4233 378/37 |
| 5,706,327 A * | 1/1998 | Adamkowski | ....... | A61B 6/0414 378/208 |
| 6,027,247 A * | 2/2000 | Tachi | ................... | A61B 6/0457 378/177 |
| 7,180,978 B2 * | 2/2007 | McKenna | ............ | A61B 6/0414 378/37 |
| 8,111,805 B2 * | 2/2012 | Standar | ................ | A61B 6/0414 378/37 |
| 8,757,876 B2 * | 6/2014 | Nakamura | ........... | A61B 6/0414 378/189 |
| 9,492,128 B2 * | 11/2016 | Lee | ....................... | A61B 6/0414 |
| 9,655,578 B2 * | 5/2017 | Nam | ....................... | A61B 6/502 |
| 9,883,846 B2 * | 2/2018 | Son | ........................ | A61B 6/4435 |
| 10,004,470 B2 * | 6/2018 | Muller | .................. | A61B 6/0414 |
| 10,130,322 B2 * | 11/2018 | Moon | ................... | A61B 6/0421 |
| 2003/0058987 A1 * | 3/2003 | Rick | .................... | A61B 6/0414 378/37 |
| 2003/0174806 A1 * | 9/2003 | Francke | ................ | A61B 6/032 378/37 |
| 2004/0109530 A1 * | 6/2004 | Amitani | ............... | A61B 6/4216 378/37 |
| 2006/0078084 A1 * | 4/2006 | Souchay | ............... | A61B 6/032 378/21 |
| 2007/0183566 A1 * | 8/2007 | Tsujita | .................... | A61B 6/502 378/37 |
| 2008/0037704 A1 * | 2/2008 | Hoffmann | ........... | A61B 6/0414 378/37 |
| 2009/0143146 A1 * | 6/2009 | Standar | ................ | A61B 6/0414 464/36 |
| 2010/0080346 A1 * | 4/2010 | Kalender | ............. | A61B 5/4312 378/37 |
| 2010/0296626 A1 * | 11/2010 | Hibino | ..................... | A61B 6/04 378/44 |
| 2012/0020464 A1 * | 1/2012 | Matsuura | ............. | A61B 6/0414 378/208 |
| 2012/0136234 A1 * | 5/2012 | Taku | .................... | A61B 6/0435 600/407 |
| 2012/0136235 A1 * | 5/2012 | Taku | .................... | A61B 5/0095 600/407 |
| 2012/0257724 A1 * | 10/2012 | Nakamura | ........... | A61B 6/0414 378/189 |
| 2013/0251112 A1 * | 9/2013 | Taku | .................... | A61B 5/0091 378/208 |
| 2013/0301796 A1 * | 11/2013 | Kim | ....................... | A61B 6/035 378/37 |

FOREIGN PATENT DOCUMENTS

| | | |
|---|---|---|
| JP | 2003-126073 A | 5/2003 |
| JP | 2009-142301 A | 7/2009 |
| JP | 2010-179030 A | 8/2010 |
| KR | 10-2013-0077793 A | 7/2013 |
| KR | 10-1377127 B1 | 3/2014 |

OTHER PUBLICATIONS

European Patent Office, European Search Report of corresponding EP Patent Application No. 15873671.0, dated Jul. 17, 2018.

* cited by examiner

LIFTING DEVICE FOR COMPRESSION PADDLE AND X-RAY IMAGING APPARATUS INCLUDING THE SAME

CROSS REFERENCE TO RELATED APPLICATIONS

This application is a National Stage Patent Application of PCT International Patent Application No. PCT/KR2015/014234 (filed on Dec. 24, 2015) under 35 U.S.C. § 371, which claims priority to Korean Patent Application No. 10-2014-0190616 (filed on Dec. 26, 2014), the teachings of which are incorporated herein in their entireties by reference.

TECHNICAL FIELD

The present invention relates generally to a lifting device for a compression paddle and an X-ray imaging apparatus including the same. More particularly, the present invention relates to a lifting device for a compression paddle and an X-ray imaging apparatus including the same, in which it is possible to quickly manually release a compression of the compression paddle on a subject, and it is possible to precisely manually adjust a compression force of the compression paddle on the subject.

BACKGROUND ART

Of X-ray imaging apparatuses, a mammography apparatus is an apparatus that irradiates X-rays to a breast and detects the X-rays penetrating through the breast to obtain a projection image, which allows early detection of a lesion such as breast cancer through the projection image. Here, radiography is performed with the breast compressed using the compression paddle, so that a lesion such as breast cancer does not overlap with the mammary gland.

However, if an emergency occurs during x-ray imaging (that is, during the breast is compressed by the compression paddle), for example, when a power supply is interrupted, a patient may feel uneasiness with the pain due to the continuous pressure on the breast.

To solve the above problem, for example, Korean patent application publication No. 10-2013-0077793 (published Jul. 9, 2013) discloses a conventional X-ray imaging apparatus.

The conventional X-ray imaging apparatus includes an electromagnetic clutch capable of selectively interlocking/disengaging the drive of the mobile device and the movement of the compression paddle according to the power on/off, wherein the electromagnetic clutch serves to release the compression of the compression paddle on the breast in an emergency such as power failure (i.e. the power is cut off).

However, in the conventional electromagnetic clutch, it serves as a means for releasing compression in the case of a complete interruption of the power supply such as due to a power failure, but it fails to serve as the means for releasing compression in the case where it is necessary to release the compression of the compression paddle on the breast due to instability of a power supply.

Meanwhile, the conventional X-ray imaging apparatus is controlled such that a compression force of the compression paddle on the breast is determined according to a predetermined manual value or is determined based on a detection result by detecting a repulsive force of the breast.

However, the conventional X-ray imaging apparatus is problematic in that since the degree of pain experienced by the patient due to the compression of the compression paddle on the breast varies with a biometric index such as patient age, breast size, and breast density, when the compression force of the compression paddle is determined solely on the basis of the uniform manual value or the repulsive force of the breast, whereby the patient is greatly distressed by the compression of the compression paddle during the radiography, and it is impossible to obtain a clear projection image of the breast when the patient is moved due to the pain, and as a result, it is impossible to identify a breast lesion correctly.

DISCLOSURE

Technical Problem

Accordingly, the present invention has been made keeping in mind the above problems occurring in the related art, and an object of the present invention is to provide a lifting device for a compression paddle and an X-ray imaging apparatus including the same, in which it is possible to quickly manually release compression of the compression paddle on a subject when it is necessary to quickly release the compression of the compression paddle 11 on the subject due to an emergency such as a complete interruption of the power supply, for example, power failure, or an unstable power supply, and it is possible to precisely manually adjust a compression force of the compression paddle on the subject.

Technical Solution

In order to achieve the above object, according to one aspect of the present invention, there is provided a lifting device for a compression paddle, the lifting device including: a lifting belt configured to be driven by a driving unit; a lifting pulley configured to be manually rotated and engaged with the lifting belt; a lifting frame configured to mount the lifting pulley; and a compression paddle mounted to the lifting frame.

The lifting device may further include: an operation shaft provided for manual rotation of the lifting pulley; and at least one gear assembly configured to transmit torque of the operation shaft to the lifting pulley.

Axes of the operation shaft and the lifting pulley may be parallel to each other, and the gear assembly may include first and second gear assemblies configured to transmit the torque of the operation shaft to the lifting pulley.

The lifting device may further include a clutch configured to transmit or release the torque between the first gear assembly and the second gear assembly.

The first gear assembly may include a one-way power transmission gear assembly configured to transmit the torque of the operation shaft in one direction, and the second gear assembly may include a power transmitting direction changing gear assembly configured to transmit the one-way transmitted torque to the lifting pulley.

The one-way power transmission gear assembly may include: a worm gear provided on the operation shaft; and a worm wheel gear engaged with the worm gear, and the power transmitting direction changing gear assembly may include: a drive bevel gear coaxially connected with the worm wheel gear; and a driven bevel gear engaged with the drive bevel gear and coaxially connected with the lifting pulley.

The first gear assembly may include a first one-way power transmission gear assembly configured to transmit the torque of the operation shaft in one direction, and the second gear assembly may include a second one-way power transmission gear assembly configured to transmit the one-way transmitted torque to the lifting pulley.

The first one-way power transmission gear assembly may include: a first worm gear provided on the operation shaft; and a first worm wheel gear engaged with the first worm gear, and the second one-way power transmission gear assembly may include: a second worm gear coaxially connected with the first worm wheel gear; and a second worm wheel gear engaged with the second worm gear and coaxially connected with the lifting pulley.

In order to achieve the above object, according to another aspect of the present invention, there is provided an X-ray imaging apparatus including: an X-ray irradiator and an X-ray receiver; a connecting unit configured to connect the X-ray irradiator and the X-ray receiver to face each other; a compression paddle provided between the X-ray irradiator and the X-ray receiver; and a lifting device configured to be accommodated in the connecting unit and to move the compression paddle up and down between the X-ray irradiator and the X-ray receiver, wherein the lifting device includes: a lifting belt configured to be driven by a driving unit; a lifting pulley configured to be manually rotated by being engaged with the lifting belt; and a lifting frame configured such that the lifting pulley is mounted thereto and the compression paddle is connected thereto.

Advantageous Effects

A lifting device for a compression paddle and an X-ray imaging apparatus including the same according to the present invention is advantageous in that it is possible to quickly manually release compression of the compression paddle on a subject in an emergency such as a complete interruption of the power supply, for example, power failure, or even when power supply is unstable, and it is possible to precisely manually adjust a compression force of the compression paddle on the subject.

MODE FOR INVENTION

The above and other related objects and features of the invention will be apparent from a reading of the following description of the disclosure found in the accompanying drawings. Therefore, those skilled in the art (hereinafter, referred to as 'a person skilled in the art') can easily understand the present invention. In the following description of the present invention, detailed descriptions of known functions and components incorporated herein will be omitted when it may make the subject matter of the present invention unclear.

Throughout the description, it will be understood that when an element is referred to as being "coupled" or "connected" to another element, it can be directly coupled or connected to the other element or intervening elements may be present therebetween. It will be further understood that the terms "comprises", "comprising", "includes", and/or "including" when used herein, specify the presence of stated features, integers, steps, operations, elements, and/or components, but do not preclude the presence or addition of one or more other features, integers, steps, operations, elements, components, and/or groups thereof.

Reference will now be made in greater detail to exemplary embodiments of the present invention, an example of which is illustrated in the accompanying drawings.

Figure 1:
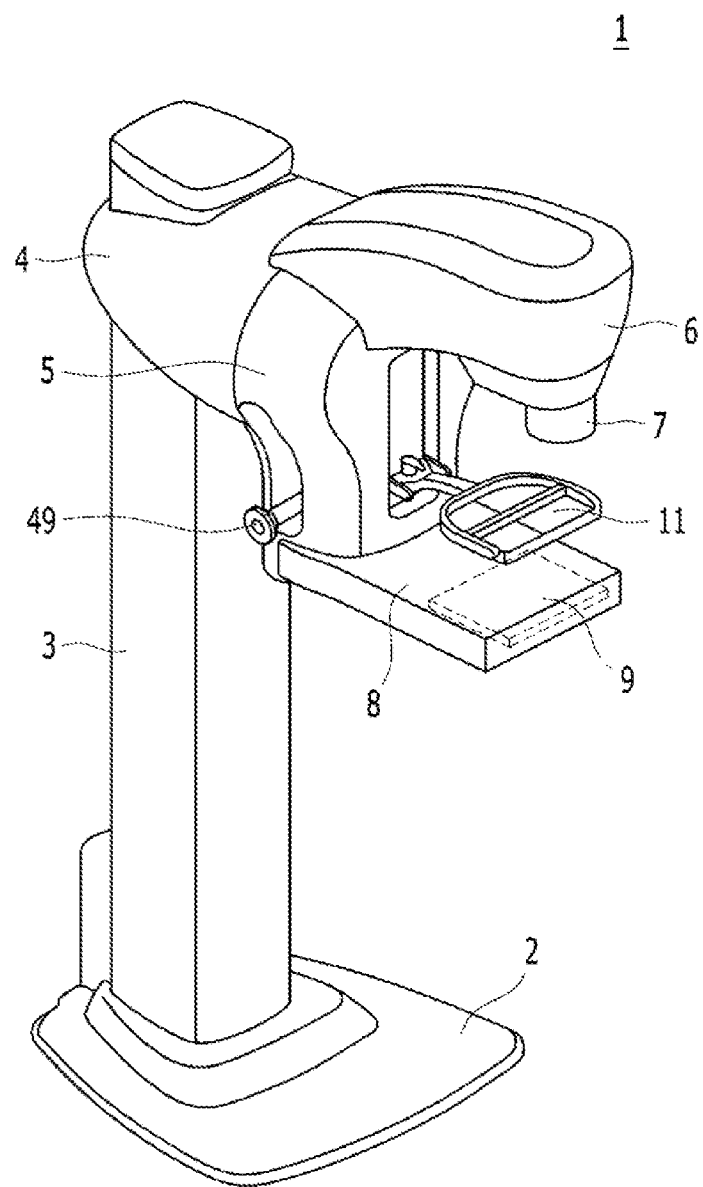
FIG. 1 is a perspective view showing an X-ray imaging apparatus according to a first embodiment of the present invention.
Figure 2:
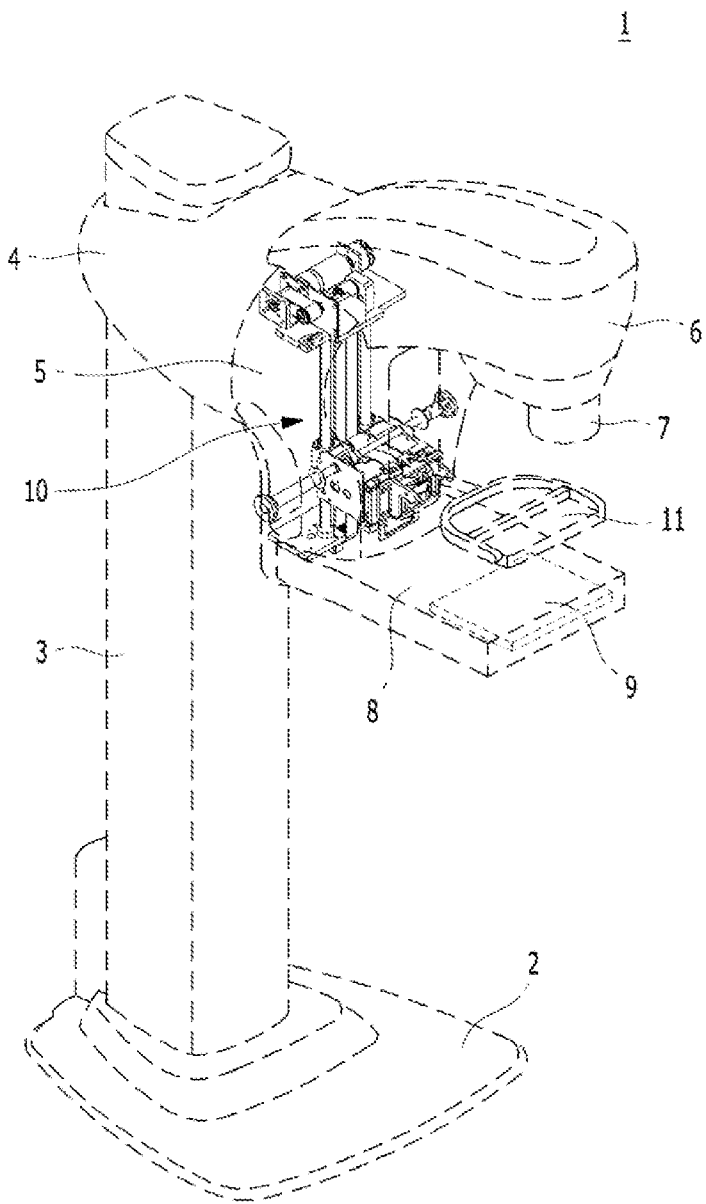
FIG. 2 is a perspective view showing the X-ray imaging apparatus provided with a lifting device for a compression paddle according to the first embodiment of the present invention.

FIG. 1 is a perspective view showing an X-ray imaging apparatus according to a first embodiment of the present invention; and FIG. 2 is a perspective view showing the X-ray imaging apparatus provided with a lifting device for a compression paddle according to the first embodiment of the present invention.

Referring to FIGS. 1 and 2, an X-ray imaging apparatus 1 according to the first embodiment of the present invention includes: a base 2; a column 3; a coupling portion 4; a connecting unit 5; an X-ray irradiator 6; an X-ray receiver 8; and a lifting device 10 for a compression paddle.

The base 2 is disposed on the installation floor to support the total load of the X-ray imaging apparatus 1.

The column 3 is a vertical column erected from the base 2, and is configured to support the X-ray irradiator 6 and the X-ray receiver 8 to face each other.

The coupling portion 4 is connected to the column 3 to be vertically movable along the column, and is configured to move the X-ray receiver 8 and the X-ray irradiator 6 up and down.

The connecting unit 5 is pivotably connected to the coupling portion 4, and is configured to pivot both the X-ray irradiator 6 and the X-ray receiver 8 around a subject (a breast) within a predetermined angle range.

The X-ray irradiator 6 is provided at an upper portion of the connecting unit 5. The X-ray irradiator 6 is provided with an X-ray source 7 that irradiates X-rays to the subject. The X-ray source 7 is a device that generates X-rays by colliding electrons having a high kinetic energy against a metal target, and is provided with a collimator configured to adjust an irradiation direction or an irradiation area of the X-rays. Here, it is preferred that the X-ray source 7 be configured to be of an electric field emission type using a nanostructure emitter, such as a carbon nanotube (CNT), but not limited thereto.

The X-ray receiver 8 is provided at a lower portion of the connecting unit 5 to face the X-ray irradiator 6. Here, the X-ray receiver 8 is provided with a detector 9 configured to detect X-rays penetrating through the subject in order to obtain a projection image.

The lifting device 10 for a compression paddle is a device that moves up and down a compression paddle 11 compressing the subject between the X-ray irradiator 6 and the X-ray receiver 8, and is accommodated in an accommodating space of the connecting unit 5 as shown in FIG. 2.

Next, a detailed description of each element of the lifting device 10 according to the present invention will be made, with reference to FIGS. 3 and 4.

Figure 3:
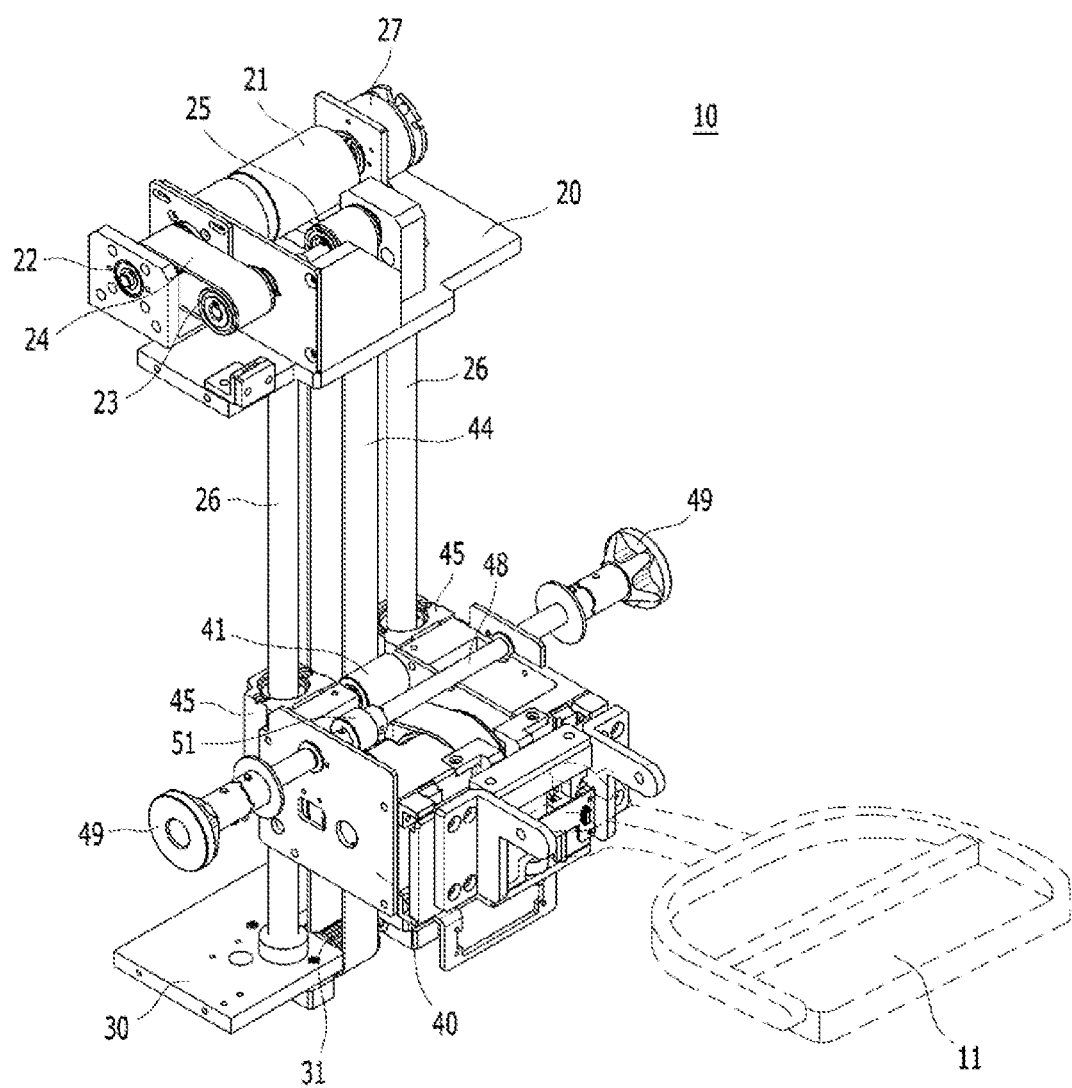
FIG. 3 is a perspective view showing the lifting device for a compression paddle of FIG. 2.
Figure 4:
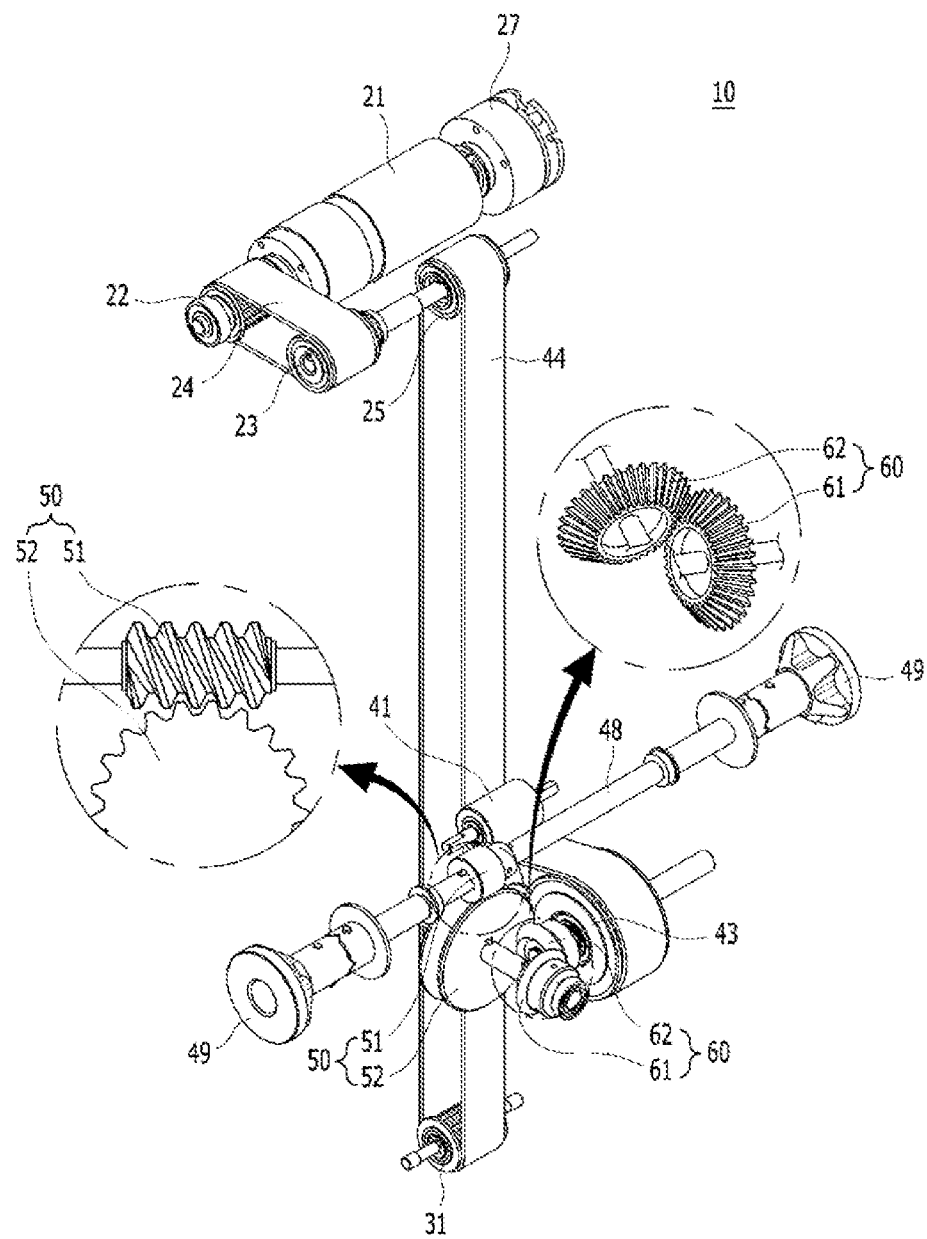
FIG. 4 is a perspective view showing main components of the lifting device for a compression paddle of FIG. 2.

FIG. 3 is a perspective view showing the lifting device for a compression paddle of FIG. 2; and FIG. 4 is a perspective view showing main components of the lifting device for a compression paddle of FIG. 2.

As shown in FIGS. 3 and 4, the lifting device 10 according to the first embodiment of the present invention includes: an upper frame 20; a lower frame 30; a lifting frame 40; a driving unit 21; a drive pulley 22; a driven pulley 23; a drive belt 24; an upper pulley 25; a lower pulley 31; a lifting pulley 43; a lifting belt 44; a one-way power transmission gear assembly 50; and a power transmitting direction changing gear assembly 60.

The driving unit 21, the drive pulley 22, the driven pulley 23, and the upper pulley 25 are mounted to the upper frame 20, and a shaft of the driven pulley 23 is rotatably supported by the upper frame.

The lower pulley 31 is mounted to the lower frame 30, and a shaft of the lower pulley 31 is rotatably supported by the lower frame.

Shafts of an upper roller 41, a lower roller (see reference numeral 42 of FIGS. 5 to 9, the same hereinafter), a lifting pulley 43, a one-way power transmission gear assembly 50, and a power transmitting direction changing gear assembly 51, 52, 61, 62 are rotatably supported by the lifting frame 40.

The upper frame 20 and the lower frame 30 are respectively installed in the accommodating space of the connecting unit 5 to be spaced apart from each other by a predetermined distance in a vertical direction; and two guide bars 26 are installed on a lower surface of the upper frame 20 and an upper surface of the lower frame 30 with the lifting belt 44 disposed therebetween, to connect the upper frame 20 and the lower frame 30.

The lifting frame 40 is provided with two guide blocks 45 each having a through-hole so as to allow the guide bar 26 to be inserted therethrough. Thereby, the lifting frame 40 is capable of sliding up and down along the guide bar 26. Further, the compression paddle 11 is installed at a front of the lifting frame 40.

The driving unit 21 is a driving source that provides a driving force moving the upper pulley 25 and the lifting belt 44, for example, it is preferred that it may be implemented as an electric motor capable of normal and reverse rotation.

The torque of the driving unit 21 is transmitted to the drive pulley 22 to rotate the drive pulley 22.

The driving belt 24 is a component that is rotated while being wound around both the drive pulley 22 and the driven pulley 23, and transmits the torque of the drive pulley 22 to the driven pulley 23 to rotate the driven pulley 23.

The torque of the driven pulley 23 is transmitted to the upper pulley 25 that is on the same shaft with the driven pulley, to rotate the upper pulley 25 clockwise or counterclockwise.

The upper pulley 25 and the lower pulley 31 are disposed to be spaced apart from each other by a predetermined distance in the vertical direction.

The lifting belt 44 is a component that is rotated while being wound around both the upper pulley 25 and the lower pulley 31, and reciprocates in the vertical direction while being rotated clockwise or counterclockwise according to clockwise or counterclockwise rotation of the upper pulley 25.

An upper roller 41 that guides the lifting belt 44 inside the lifting frame 40, a lower roller 42 that guides the lifting belt 44 outside the lifting frame 40, and a lifting pulley 43 that the lifting belt 44 guided inside the lifting frame 40 is wound around are respectively mounted to the lifting frame 40.

Further, an operation shaft 48 is rotatably supported by the lifting frame 40 and each ends of the operation shaft 48 is provided with a knob 49 so that an operator can manipulate the operation shaft 48 by rotating the knob 49 clockwise or counterclockwise. Here, an axial direction of the operation shaft 48 is arranged to be parallel to an axial direction of the lifting pulley 43.

The torque of the operation shaft 48 is transmitted sequentially to the one-way power transmission gear assembly 50, the power transmitting direction changing gear assembly 60, and the lifting pulley 43.

Here, for precise transmission of the torque, it is preferred that each of the drive belt 24 and the lifting belt 44 may be implemented as a timing belt, and each of the drive pulley 22, the driven pulley 23, the upper pulley 25, the lower pulley 31, and the lifting pulley 43 may be implemented as a timing pulley.

The one-way power transmission gear assembly 50, as an arbitrary first gear assembly, may be implemented, for example, as a worm gear 51 and a worm wheel gear 52; and the power transmitting direction changing gear assembly 60, as an arbitrary second gear assembly, may be implemented, for example, as a drive bevel gear 61 and a driven bevel gear 62. The above configuration of the gear assembly is provided as an example, so the configuration is not limited thereto, and may also be implemented with other gear assemblies that perform similar functions.

As shown in FIG. 4, when the worm gear 51 provided on the operation shaft 48 is rotated clockwise or counterclockwise, the worm wheel gear 52 engaged with the worm gear 51 is rotated clockwise or counterclockwise. As a result, the torque of the worm gear 51 is transmitted to the worm wheel gear 52.

However, due to the nature of the engagement between the worm gear 51 and the worm wheel gear 52, the torque of the worm wheel gear 52 is locked in a reverse direction without being transmitted to the worm gear 51. As a result, the torque is transmitted from the worm gear 51 to the worm wheel gear 52 in one direction, and it is not transmitted from the worm wheel gear 52 to the worm gear 51.

The drive bevel gear 61 is connected to the operation shaft 48 that is on the same axis as the worm wheel gear 52. Accordingly, the torque transmitted from the worm gear 51 to the worm wheel gear 52 is transmitted to the drive bevel gear 61 that is on the same shaft with the worm wheel gear 52, thereby rotating the drive bevel gear 61 clockwise or counterclockwise.

When the drive bevel gear 61 is rotated clockwise or counterclockwise, the driven bevel gear 62 engaged with the drive bevel gear 61 is rotated clockwise or counterclockwise. As a result, the torque direction of the drive bevel gear 61 is changed by about 90 degrees, and the torque is transmitted to the driven bevel gear 62.

The driven bevel gear 62 is connected with the lifting pulley 43. Accordingly, the torque transmitted to the driven bevel gear 62 is transmitted to the lifting pulley 43 that is on the same shaft with the driven bevel gear, thereby rotating the lifting pulley 43 clockwise or counterclockwise.

Next, the lifting device 10 for a compression paddle according to a second embodiment of the present invention will be described with reference to FIG. 5. Here, in describing the lifting device 10 for a compression paddle according to another embodiment of the present invention, the description of the same components as the lifting device according to an embodiment of the present invention will be skipped, and reference will be made in detail to the lifting device, rather, the different components will be described in detail.

Figure 5:
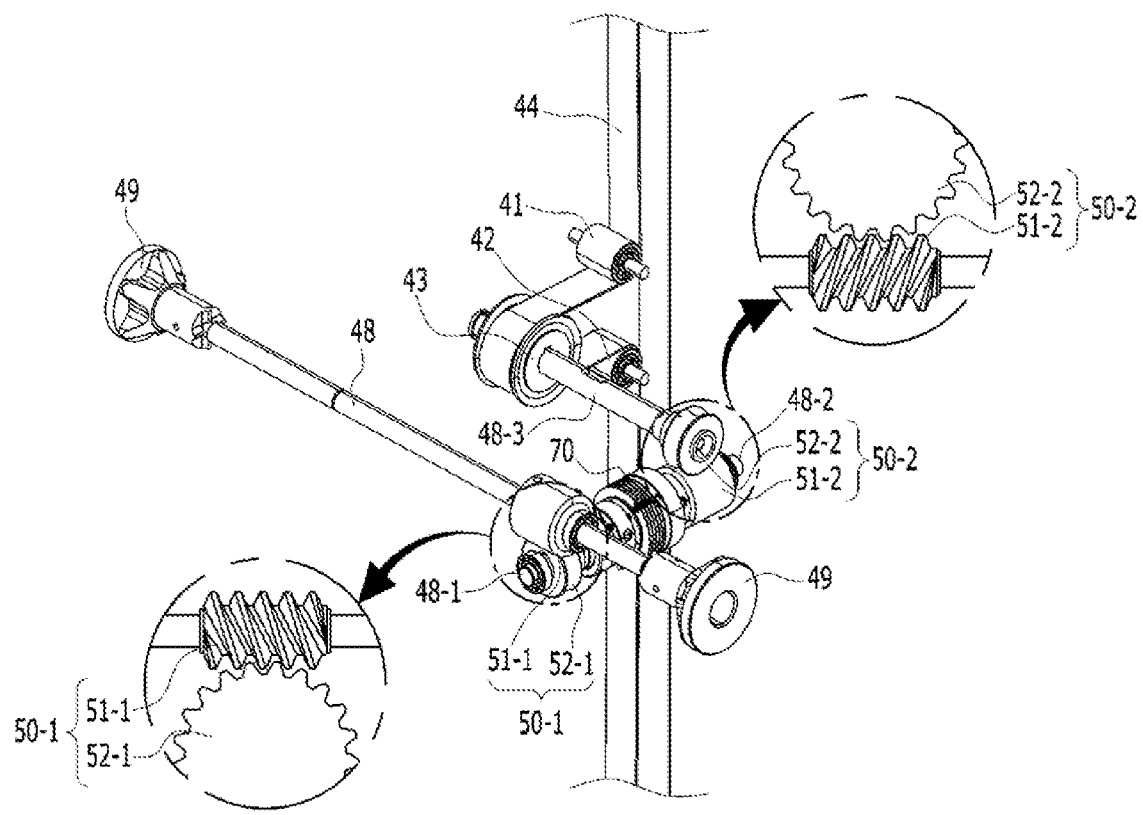
FIG. 5 is a perspective view showing a lifting device for a compression paddle according to a second embodiment of the present invention.

Referring to FIG. 5, the lifting device 10 for a compression paddle according to the second embodiment of the present invention includes an operation shaft 48, a first one-way power transmission gear assembly 50-1, a second one-way power transmission gear assembly 50-2, and a clutch 70.

The operation shaft 48 is a component that is rotatably supported by the lifting frame 40; and each ends of the operation shaft 48 is provided with a knob 49, so that an operator can rotate the operation shaft 48 clockwise or counterclockwise by using the knob 49 that is provided at each ends of the operation shaft. Here, the axial direction of the operation shaft 48 is arranged to be parallel to the axial direction of the lifting pulley 43.

The first one-way power transmission gear assembly 50-1 is provided with a first worm gear 51-1 which is fixedly mounted on the operation shaft 48 and a first worm wheel gear 52-1 fixedly mounted on a drive shaft 48-1, respectively.

Accordingly, when the operation shaft 48 is rotated clockwise or counterclockwise, the first worm gear 51-1 is rotated clockwise or counterclockwise, and the first worm wheel gear 52-1 engaged with the first worm gear 51-1 is rotated clockwise or counterclockwise along with the drive shaft 48-1.

Here, due to the nature of the engagement between the first worm gear 51-1 and the first worm wheel gear 52-1, torque is transmitted from the first worm gear 51-1 to the first worm wheel gear 52-1 in one direction, and it is locked in a reverse direction without being transmitted from the first worm wheel gear 52-1 to the first worm gear 51-1.

The second one-way power transmission gear assembly 50-2 is provided with a second worm gear 51-2 fixedly mounted on a driven shaft 48-2 and a second worm wheel gear 52-2 fixedly mounted on a lifting shaft 48-3, respectively.

Accordingly, when the driven shaft 48-2 is rotated clockwise or counterclockwise, the second worm gear 51-2 is rotated clockwise or counterclockwise, and the second worm wheel gear 52-2 engaged with the first worm gear 51-2 is rotated clockwise or counterclockwise along with the lifting shaft 48-3.

Here, due to the nature of the engagement between second worm gear 51-2 and the second worm wheel gear 52-2, torque is transmitted from the second worm gear 51-2 to the second worm wheel gear 52-2 in one direction, and it is locked in a reverse direction without being transmitted from the second worm wheel gear 52-2 to the second worm gear 51-2.

The clutch 70 is a component that connects or disconnects the drive shaft 48-1 and the driven shaft 48-2, and serves to block torque by disconnecting the drive shaft 48-1 and the driven shaft 48-2 when the torque applied to the drive shaft 48-1 is greater than or equal to a predetermined value. Accordingly, it is possible to prevent the compression paddle 11 from excessively compressing the breast by preventing excessive torque from being applied to the drive shaft 48-1.

Further, since the first and second one-way power transmission gear assemblies 50-1 and 50-2 are disposed with the clutch 70 therebetween, it is possible to prevent the lifting device 10 from being moved down by self-weight while the drive and driven shafts 48-1 and 48-2 are connected with or disconnected from each other.

For reference, the clutch 70 according to the first embodiment may be applied to the first embodiment, wherein preferably, the clutch transmits or blocks torque between the first gear assembly and the second gear assembly, and to achieve this, for example, the clutch can connect or disconnect shafts between the worm wheel gear 52 and the drive bevel gear 61.

Reference will be made to the operational state of main components of the lifting device 10 for moving the compression paddle 11 up and down, with reference to FIGS. 6 and 7.

Figure 6:
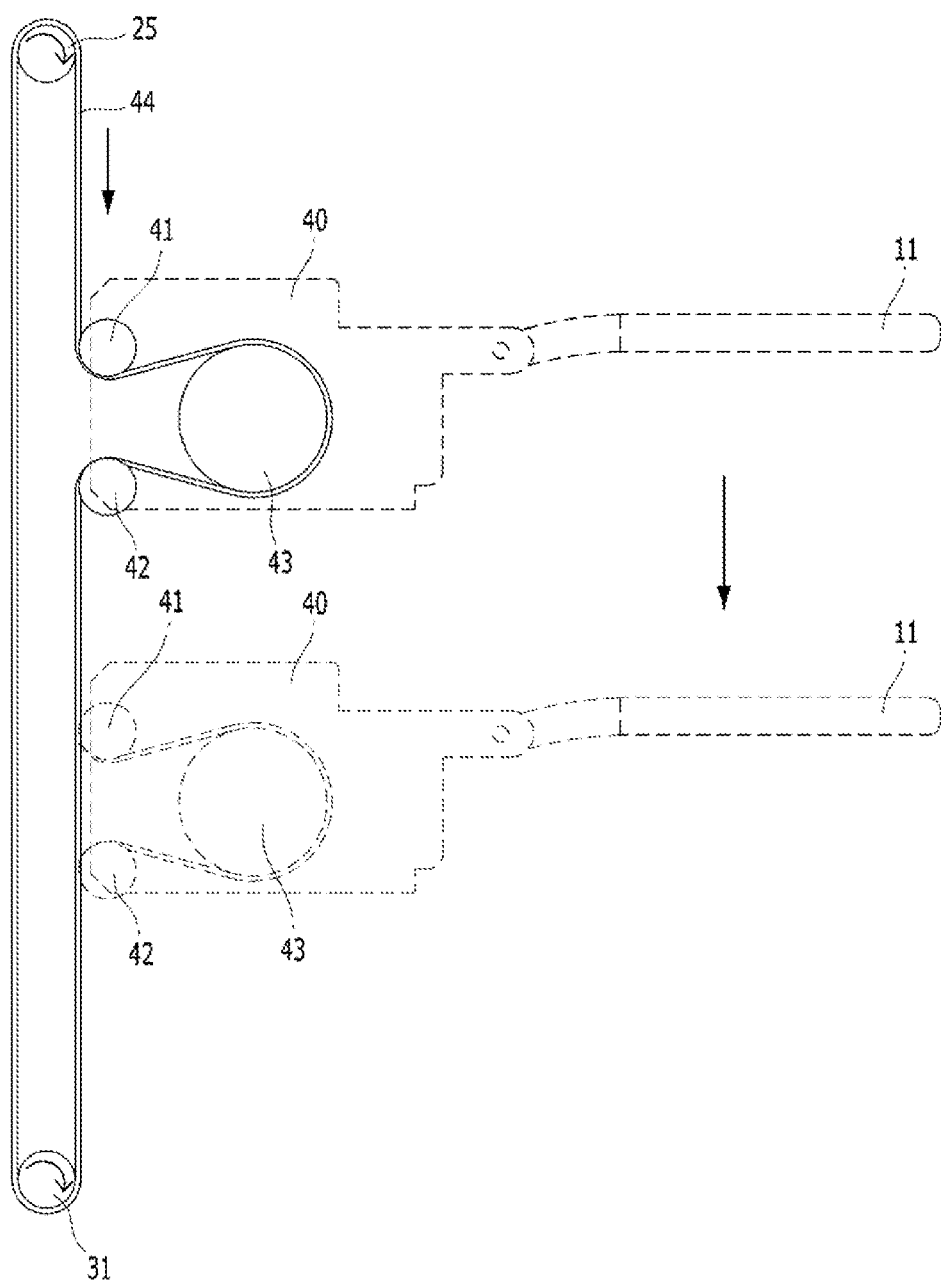
FIG. 6 is a schematic view showing an operational state of main components of the lifting device for a compression paddle while the compression paddle is moved down.
Figure 7:
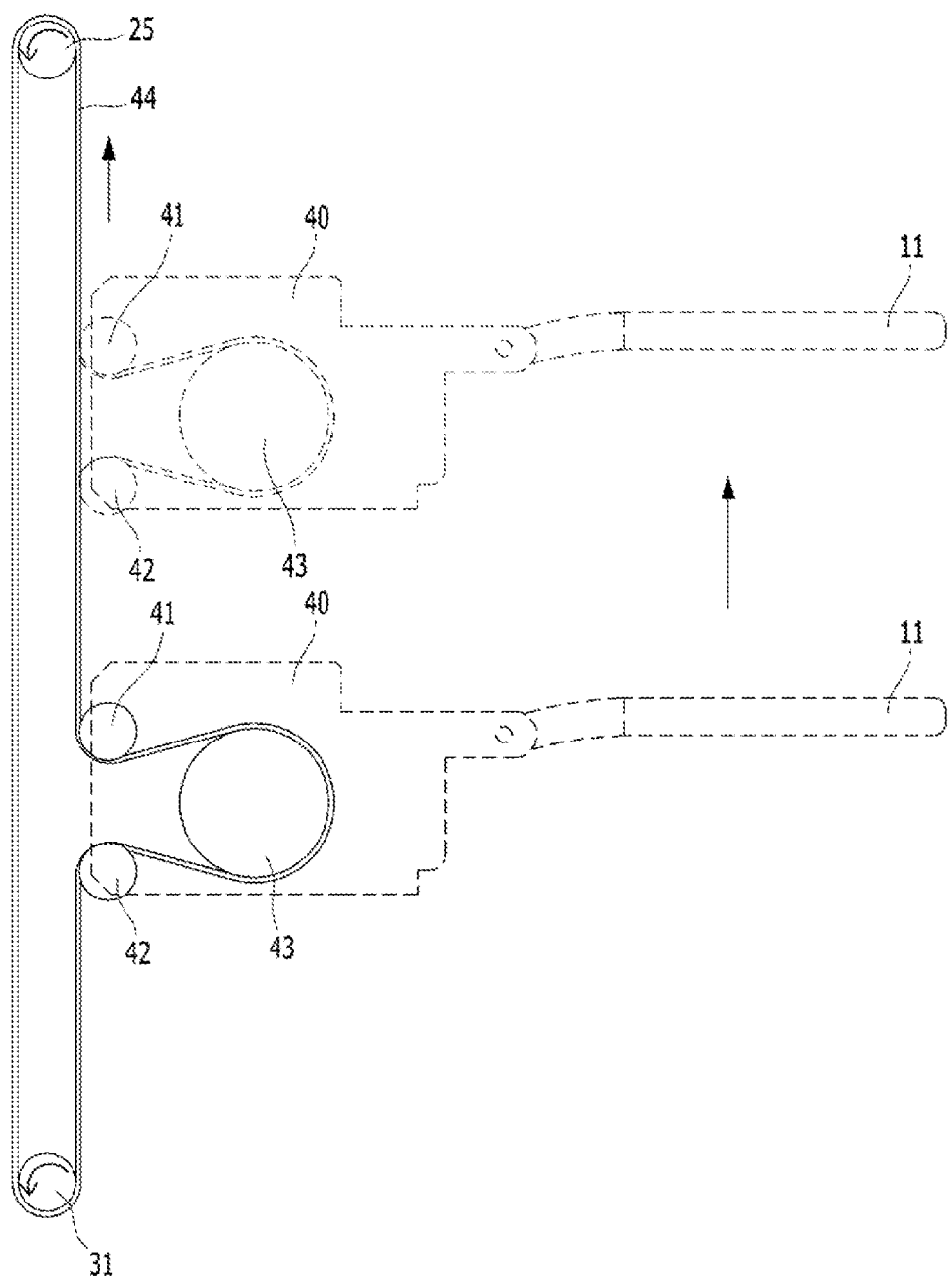
FIG. 7 is a schematic view showing an operational state of main components of the lifting device for a compression paddle while the compression paddle is moved up.

FIG. 6 is a schematic view showing an operational state of main component of the lifting device for a compression paddle while the compression paddle is moved down; and FIG. 7 is a schematic view showing an operational state of main components of the lifting device for a compression paddle while the compression paddle is moved up.

Referring to FIG. 6, the torque of the driving unit 21 is transmitted sequentially to the drive pulley 22, the driving belt 24, the driven pulley 23, and the upper pulley 25, whereby the upper pulley 25 is rotated clockwise. Thereby, the lifting belt 44 wound around the upper pulley 25 and the lower pulley 31 is moved down while being rotated clockwise. Here, since the lifting pulley 43 is locked by the one-way power transmission gear assembly 50, it is maintained in a non-rotating state, whereby as the lifting belt 44 is moved down, the lifting pulley 43 is moved down along with the lifting belt 44, and accordingly, the compression paddle 11 is also moved down.

Referring to FIG. 7, when the upper pulley 25 is rotated counterclockwise by the driving unit 21, the lifting belt 44 is moved up while being rotated counterclockwise. Also in this case, the lifting pulley 43 is locked by the one-way power transmission gear assembly 50, being maintained in a non-rotating state, whereby as the lifting belt 44 is moved up, the lifting pulley 43 is moved up along with the lifting belt 44, and accordingly, the compression paddle 11 is also moved up.

Reference will be made to the operational state of main components of the lifting device 10 for releasing (or relieving) or further increasing compression of the compression paddle 11 on the subject, with reference to FIGS. 8 and 9.

Figure 8:
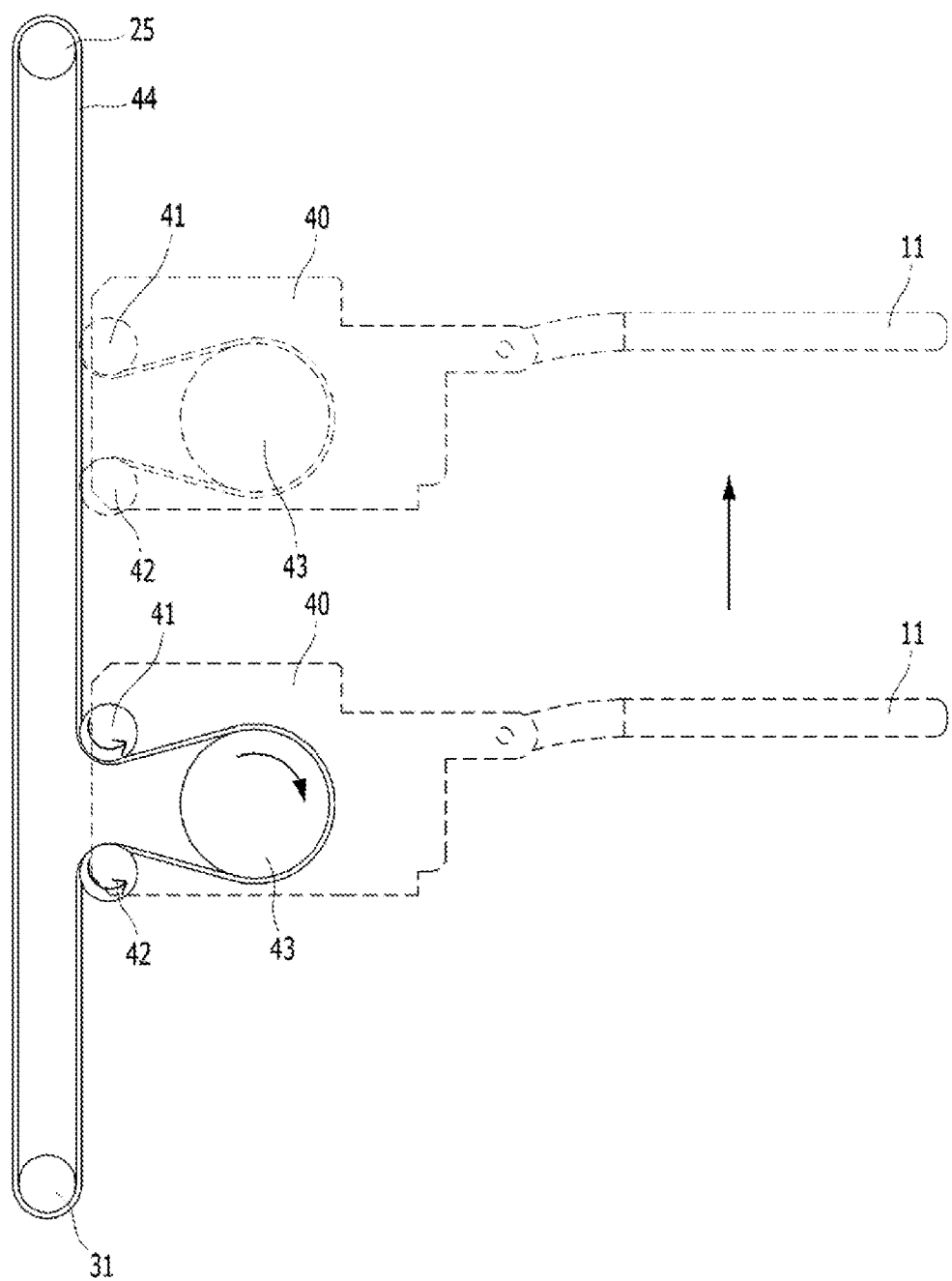
FIG. 8 is a schematic view showing an operational state of main components of the lifting device for a compression paddle while releasing or relieving compression of the compression paddle on a subject.
Figure 9:
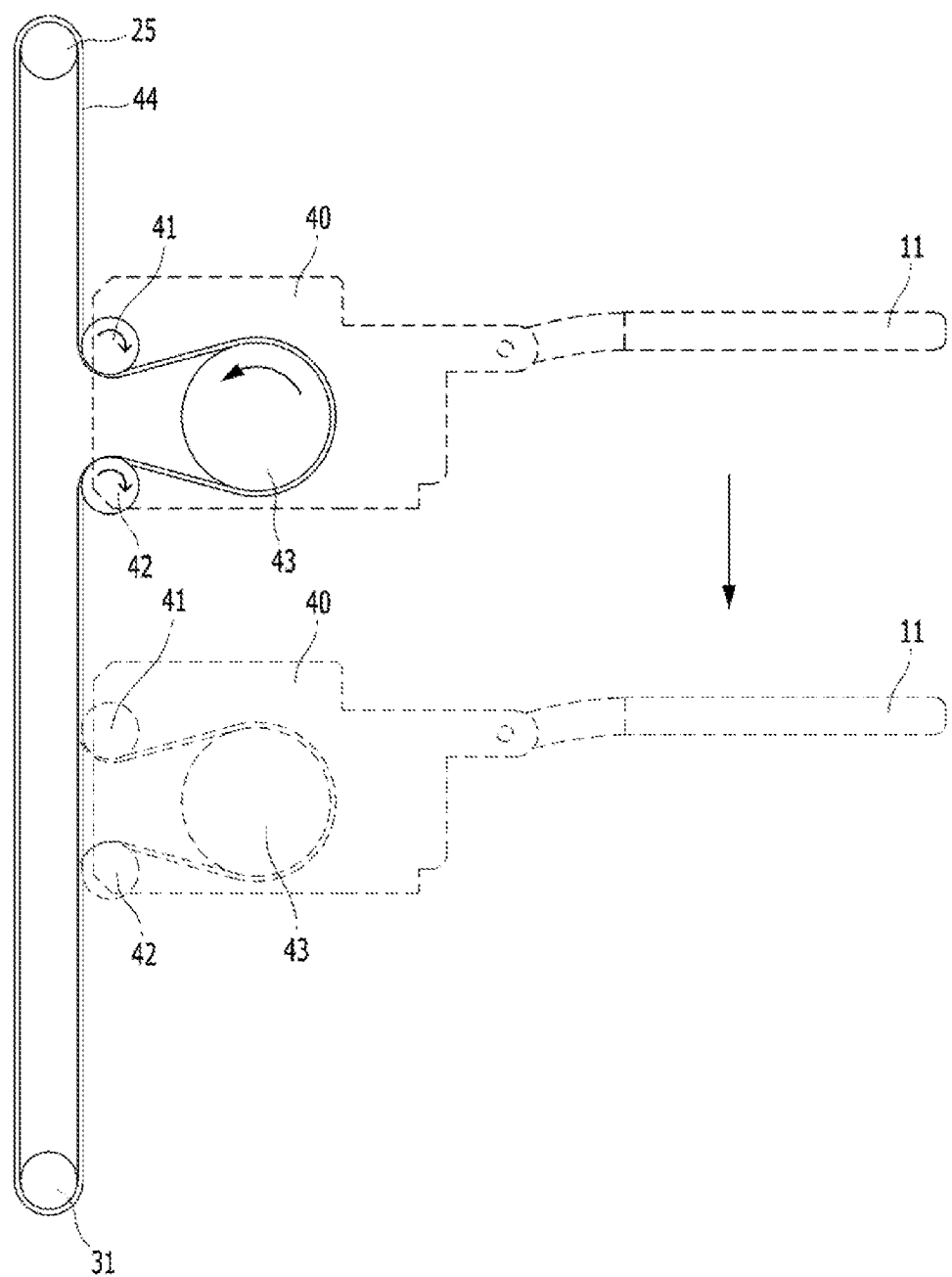
FIG. 9 is a schematic view showing an operational state of main components of the lifting device for a compression paddle while increasing compression of the compression paddle on a subject.

FIG. 8 is a schematic view showing an operational state of main components of the lifting device for a compression paddle while releasing or relieving compression of the compression paddle on a subject; and FIG. 9 is a schematic view showing an operational state of main components of the lifting device for a compression paddle while increasing compression of the compression paddle on a subject.

Referring to FIGS. 8 and 9, when compression of the compression paddle 11 on the subject is completed, the upper pulley 25 is maintained in a non-rotating state by being locked by an electric break 27 connected to the driving unit 21, whereby the lifting belt 44 is also held in place without rotation. In the state where the lifting belt 44 remains in place, when the operator rotates the knob 49 of the operation shaft 48 clockwise or counterclockwise, the torque is transmitted sequentially to the one-way power transmission gear assembly 50, the power transmitting direction changing gear assembly 60, and the lifting pulley 43, whereby the lifting pulley 43 is rotated clockwise or counterclockwise.

While rotated clockwise or counterclockwise, the lifting pulley 43 is moved up or down along the lifting belt 44 that is held in place without rotation, and as a result, the compression paddle 11 is moved up or down along therewith. Accordingly, it is possible for the operator to release (or relieve) or further increase compression of the compression paddle 11 on the subject.

Reference will now be made to how to radiograph the subject (the breast) of an examinee using the X-ray imaging apparatus 1 according to the present invention.

Firstly, when the examinee enters the imaging location of the X-ray imaging apparatus 1 with a standing or sitting position, the operator moves the coupling portion 4 up and down along the column 3 to adjust the height of the X-ray receiver 8, such that the breast of the examinee is placed on the X-ray receiver 8.

Then, the operator moves down the compression paddle 11 disposed between the X-ray irradiator 6 and the X-ray receiver 8 to compress the breast of the examinee. When the compression of the compression paddle 11 on the breast is completed, the compression paddle 11 is locked by the electric break 27.

During the radiography (that is, during the compression on the breast by the compression paddle), if it is determined that it is necessary to quickly release the compression of the compression paddle 11 on the breast due to an emergency such as a complete interruption of the power supply (e.g., power failure) or instability of a power supply, the operator manually rotates the knob 49 of the operation shaft 18 clockwise to move up the compression paddle 11, whereby it is possible to quickly release the compression of the compression paddle 11 on the breast.

If the examinee determines that it is necessary to relieve the compression of the compression paddle 11 due to the examinee suffering a great deal of pain caused by the compression on the breast or determines that it is necessary to further increase a compression force of the compression paddle 11 on the breast to obtain a clearer projection image, the operator rotates the knob 49 of the operation shaft 18 clockwise or counterclockwise as necessary, whereby it is possible to precisely relieve or increase the compression force of the compression paddle 11 on the breast.

After the compression force of the compression paddle 11 on the breast of the examinee is precisely adjusted by using the lifting device 10 according to the present invention, the operator performs radiography of the breast while pivoting the connecting unit 5 to move the X-ray irradiator 6 and the X-ray receiver 8 to imaging locations according to a craniocaudal (CC) view (a top-down view), a mediolateral-oblique (MLO) view (an angled view) and/or a mediolateral (ML) view (a center-outward view).

Here, the radiography is performed in a manner such that the X-ray source 7 of the X-ray irradiator 6 irradiates X-rays to the breast, and the detector 9 of the X-ray receiver 8 receives the X-rays penetrating through the breast, wherein the detector 9 generates an electric signal for each position proportional to the incident amount of the received X-ray, reads the electric signal and the position information, and processes them by an image processing algorithm, thereby generating a projection image of the breast according to the CC view, the MLO view and/or the ML view.

Hereinbefore, it has been described that the X-ray imaging apparatus according to the embodiment of the present invention is used as a mammography apparatus for imaging a breast, but the present invention is not limited thereto. In other words, the X-ray imaging apparatus according to the present invention is applicable to all the types of X-ray imaging apparatuses that perform radiography to obtain a projection image of a subject while compressing the subject, and it will be appreciated by those skilled in the art that the technical scope of the present invention extends to such types of X-ray imaging apparatuses.

Further, the embodiments disclosed in the present invention are not restrictive but are illustrative. In other words, it is understood by those skilled in the art that various changes and modifications may be made in the invention without departing from the spirit and scope thereof. Therefore, the scope of the present invention should be interpreted by the accompanying claims, and it is to be understood that all technical ideas within the claims fall within the purview of the present invention.

The invention claimed is:

1. A lifting device for a compression paddle, the lifting device comprising:
   a lifting belt configured to be driven by a driving unit;
   a lifting pulley configured to be manually rotated and engaged with the lifting belt;
   a lifting frame configured to mount the lifting pulley;
   a compression paddle mounted to the lifting frame;
   an operation shaft provided for the manual rotation of the lifting pulley; and
   at least one gear assembly configured to transmit a torque of the operation shaft to the lifting pulley,
   wherein the compression paddle is moved by the manual rotation of the lifting pulley along the belt or by the movement of the lifting belt while the lifting pulley is in non-rotating state, and
   wherein axes of the operation shaft and the lifting pulley are parallel to each other, and the at least one gear assembly includes a first gear assembly and a second gear-assembly.

2. The lifting device of claim 1, further comprising:
   a clutch configured to transmit or release the torque between the first gear assembly and the second gear assembly.

3. The lifting device of claim 1, wherein the first gear assembly includes a one-way power transmission gear assembly configured to transmit the torque of the operation shaft in one direction, and
   the second gear assembly includes a power transmitting direction changing gear assembly configured to transmit the one-way transmitted torque to the lifting pulley.

4. The lifting device of claim 3, wherein the one-way power transmission gear assembly includes a worm gear provided on the operation shaft and a worm wheel gear engaged with the worm gear, and
   the power transmitting direction changing gear assembly includes a drive bevel gear coaxially connected with the worm wheel gear and a driven bevel gear engaged with the drive bevel gear and coaxially connected with the lifting pulley.

5. The lifting device of claim 1, wherein the first gear assembly includes a first one-way power transmission gear assembly configured to transmit the torque of the operation shaft in one direction, and the second gear assembly includes a second one-way power transmission gear assembly configured to transmit the one-way transmitted torque to the lifting pulley.

6. The lifting device of claim 5, wherein the first one-way power transmission gear assembly includes a first worm gear provided on the operation shaft and a first worm wheel gear engaged with the first worm gear, and the second one-way power transmission gear assembly includes a second worm gear coaxially connected with the first worm wheel gear and a second worm wheel gear engaged with the second worm gear and coaxially connected with the lifting pulley.

7. The lifting device of claim 1, wherein the lifting frame includes rollers to guide the lifting belt.

8. The lifting device of claim 1, wherein the at least one gear assembly configured to transmit the torque in one direction.

9. The lifting device of claim 1, wherein the at least one gear assembly configured to change a transmission direction of the torque.

10. An X-ray imaging apparatus comprising:
an X-ray irradiator and an X-ray receiver;
a connecting unit configured to connect the X-ray irradiator and the X-ray receiver to face each other;
a compression paddle provided between the X-ray irradiator and the X-ray receiver; and
a lifting device configured to be accommodated in the connecting unit and to move the compression paddle up and down between the X-ray irradiator and the X-ray receiver,
wherein the lifting device includes:
a lifting belt configured to be driven by a driving unit;
a lifting pulley configured to be manually rotated and engaged with the lifting belt;
a lifting frame configured to mount the lifting pulley and be connected to the compression paddle;
an operation shaft provided for the manual rotation of the lifting pulley; and
at least one gear assembly configured to transmit a torque of the operation shaft to the lifting pulley,
wherein the compression paddle is moved by the manual rotation of the lifting pulley along the belt or by the movement of the lifting belt while the lifting pulley is in non-rotating state, and
wherein axes of the operation shaft and the lifting pulley are parallel to each other, and the at least one gear assembly is configured to transmit the torque in one direction.

11. The X-ray imaging apparatus of claim 10, further comprising:
a clutch configured to transmit or release the torque between the first gear assembly and the second gear assembly.

* * * * *